(12) United States Patent
Takaki et al.

(10) Patent No.: US 8,053,570 B2
(45) Date of Patent: Nov. 8, 2011

(54) METHOD FOR PRODUCING α-FORM TITANYLPHTHALOCYANINE AND ELECTROPHOTOGRAPHIC PHOTORECEPTOR COMPRISING α-FORM TITANYLPHTHALOCYANINE

(75) Inventors: Kenji Takaki, Neyagawa (JP); Yasuhiro Yamasaki, Neyagawa (JP)

(73) Assignee: Orient Chemical Industries, Ltd., Osaka-Shi, Osaka-Fu (JP)

( * ) Notice: Subject to any disclaimer, the term of this patent is extended or adjusted under 35 U.S.C. 154(b) by 669 days.

(21) Appl. No.: 12/177,738

(22) Filed: Jul. 22, 2008

(65) Prior Publication Data
US 2009/0042116 A1    Feb. 12, 2009

(30) Foreign Application Priority Data
Aug. 2, 2007  (JP) .................................. 2007-202034

(51) Int. Cl.
C09B 67/12    (2006.01)
(52) U.S. Cl. ........................................................ 540/141
(58) Field of Classification Search .................... 540/141
See application file for complete search history.

(56) References Cited

FOREIGN PATENT DOCUMENTS

| EP | 1972634 A1 | 9/2008 |
|----|-----------|--------|
| JP | 61-239248 A | 10/1986 |
| JP | 8-209023 A | 8/1996 |
| JP | 11-21466 A | 1/1999 |

Primary Examiner — James O Wilson
Assistant Examiner — Brian McDowell
(74) Attorney, Agent, or Firm — Birch, Stewart, Kolasch & Birch, LLP (57) ABSTRACT

The present invention relates to a method for producing an α-form titanylphthalocyanine represented by the formula (1):

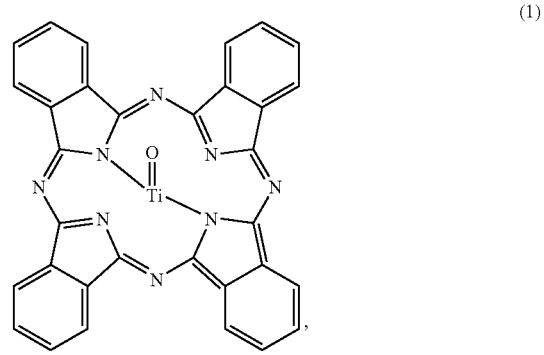

(1)

which has a peak at a Bragg angle (2θ±0.2°) in X-ray diffraction spectrum with CuK α-ray: 7.5°, 10.2°, 12.6°, 13.2°, 15.1°, 16.3°, 17.3°, 18.3°, 22.5°, 24.2°, 25.3° and 28.6°, wherein the method includes steps of:

(I) subjecting a crude titanylphthalocyanine having an α-form polymorph to an acid pasting treatment, and then filtering and washing with water to give a water-containing wet cake, and then subjecting the wet cake to drying and crushing to give a low crystalline titanylphthalocyanine;

(II) adding a dispersing aid to the low crystalline titanylphthalocyanine and dispersing at room temperature, in DMF, to prepare a polymorph; and (III) filtering, washing, and drying under a reduced pressure.

2 Claims, 5 Drawing Sheets

METHOD FOR PRODUCING α-FORM TITANYLPHTHALOCYANINE AND ELECTROPHOTOGRAPHIC PHOTORECEPTOR COMPRISING α-FORM TITANYLPHTHALOCYANINE

TECHNICAL FIELD

The present invention relates to a method for producing an α-form titanylphthalocyanine and an electrophotographic photoreceptor comprising a charge generating material of the α-form titanylphthalocyanine.

BACKGROUND OF THE INVENTION

In image-formation apparatuses, such as photocopiers and printers, to which electrophotographic technologies are applied, many organic photoreceptors are employed, each of which has a sensitivity to light emitted from a light-source in the apparatus within a range of wavelength of the light. It is known that the organic photoreceptor includes monolayer type photoreceptors and multilayer type photoreceptors. The monolayer type photoreceptor comprises a single photoreceptor layer wherein a charge generating material and a charge transferring material have been dispersed in a thin film of an appropriate binder resin. The multilayer type photoreceptor comprises a charge generating layer comprising a charge generating material; and a charge transferring layer comprising a charge transferring material, wherein the charge generating layer and the charge transferring layer are laminated.

Conventional phthalocyanine compound has a spectral sensitivity to a light having a long wavelength or less, good charge generation efficiency, good fastness, high sensitivity and high durability. Therefore, various phthalocyanine compounds are employed as charge generating materials. Among others, titanylphthalocyanine can be used in an electrophotographic photoreceptor, since the titanylphthalocyanine has characteristics such as high charging amount and high sensitivity, and the titanylphthalocyanine can be easily formed into a thin film, such as a charge generating layer, by vapor deposition or dispersing.

These phthalocyanine compounds have considerably different electric characteristics depending on each stacking state even though they have the same molecular structure. Stacking state of the organic compound molecule is determined by its polymorph. Therefore, different polymorph provides different stacking state. Accordingly, perturbation of electron in π electron system is altered. This is why that the characteristics in an electronic material such as an organic photoreceptor can be significantly altered.

Generally, titanylphthalocyanines can be produced by an urea synthetic method (i.e., Weiller method) or a phthalonitrile synthetic method. These conventional methods, however, immediately after the synthesis, often provide a crude titanylphthalocyanines containing various polymorphs, such as "β-form", "α-form" and other metastable polymorphs, i.e., a polymorphic mixture. Since the polymorphic mixture is a mixture of crystals each of which has different electric characteristics, the conventional titanylphthalocyanines are not suitable for applying them to a charge generating material such as an electrophotographic photoreceptor.

Therefore, in the art, titanylphthalocyanine having a suitable single polymorph has been investigated in order to use the titanylphthalocyanine, as starting material, as it is a crude, suitable for producing a charge generating material. Examples of such attempts include the followings.

Patent Literature 1: JP-A-61-239248 discloses a method for producing an α-form titanylphthalocyanine having a peak at a Bragg angle (2θ±0.2°) in X-ray diffraction spectrum with CuK α-ray: 7.5°, 12.3°, 16.3°, 25.3° and 28.7°, which includes preparation of a crude α-form titanylphthalocyanine according to a phthalonitrile synthetic method; washing the crude titanylphthalocyanine with acetone by means of a Soxhlet's extractor; dry milling the washed titanylphthalocyanine in the presence of alumina beads. This method employs a Soxhlet's extractor. Therefore, the equipments for the synthesis are complicated. The method includes vigorous washing with a solvent with heating. Therefore, such procedure is complicated. Totally, the disclosed method is not a convenient for producing an α-form titanylphthalocyanine.

Patent Literature 2: JP-A-8-209023 discloses a method of transformation including subjecting a low crystalline titanylphthalocyanine resulted from an acid pasting treatment to milling with zirconia beads in the presence of dichlorotoluene, sodium chloride and water to prepare a crystal thereof having a peak at a Bragg angle (2θ±0.2°) in X-ray diffraction spectrum with CuK α-ray: 7.22°, 9.60°, 11.60°, 13.40°, 14.88°, 18.34°, 23.62°, 24.14° and 27.32°. This method, however, includes a complicated steam distillation in order to remove the dichlorotoluene. There may be a problem that the resulting photosensitive characteristics of the titanylphthalocyanine are deteriorated, if the resulting titanylphthalocyanine is contaminated with any inorganic salt such as sodium chloride. Therefore, many water-washing procedures are required. Totally, the disclosed method is complicated.

SUMMARY OF THE INVENTION

Disclosure of the Invention

Problem to be Solved by the Invention

The present inventors have intensively investigated in order to solve the problems in the above-described prior arts. Therefore, objects of the present invention consist in a provision (hereinafter, which is referred to as a first object) of a method for conveniently producing an α-form titanylphthalocyanine having a peak at a Bragg angle (2θ±0.2°) in X-ray diffraction spectrum with CuK α-ray: 7.5°, 10.2°, 12.6°, 13.2°, 15.1°, 16.3°, 17.3°, 18.3°, 22.5°, 24.2°, 25.3° and 28.6°, wherein a crude titanylphthalocyanine having an α-form polymorph is used as a starting material, and a provision (hereinafter, which is referred to as a second object) of an electrophotographic photoreceptor comprising a charge Generating material of the α-form titanylphthalocyanine, which has excellent photosensitive characteristics.

Means for Solving the Problem

The present inventors have intensively investigated in order to solve the above-described problems and found that a method, which includes an acid pasting treatment of a crude titanylphthalocyanine having an α-form polymorph; filtering and water-washing; drying and crushing to provide a low crystalline titanylphthalocyanine; and dispersing, at room temperature, of the resulting low crystalline titanylphthalocyanine under mild conditions, can conveniently provide only an α-form titanylphthalocyanine. Accordingly, the present invention can provide followings.

A method for producing an α-form titanylphthalocyanine represented by the formula (1):

(1)

which has a peak at a Bragg angle (2θ±0.2°) in X-ray diffraction spectrum with CuK α-ray: 7.5°, 10.2°, 12.6°, 13.2°, 15.1°, 16.3°, 17.3°, 18.3°, 22.5°, 24.2°, 25.3° and 28.6°, wherein the method includes steps of:

(I) subjecting a crude titanylphthalocyanine having an α-form polymorph to an acid pasting treatment, and then filtering and washing with water to give a water-containing wet cake, and then subjecting the wet cake to drying and crushing to give a low crystalline titanylphthalocyanine;

(II) adding a dispersing aid to the low crystalline titanylphthalocyanine and dispersing at room temperature, in DMF (dimethylformamide), to prepare a polymorph; and (III) filtering, washing, and drying under a reduced pressure.

According to the above-described present inventive method for producing the α-form titanylphthalocyanine, it is preferable that the low crystalline titanylphthalocyanine has a peak at a Bragg angle (2θ±0.2°) in X-ray diffraction spectrum with CuK α-ray: 7.0°, 15.6°, 23.5° and 28.4°.

The present invention can further provide an electrophotographic photoreceptor comprising a charge generating material of the α-form titanylphthalocyanine obtained/obtainable by the above-described production method.

Effect of the Invention

The present invention can provide a method for conveniently producing the α-form titanylphthalocyanine having a peak at a Bragg angle (2θ±0.2°) in X-ray diffraction spectrum with CuK α-ray: 7.5°, 10.2°, 12.6°, 13.2°, 15.1°, 16.3°, 17.3°, 18.3°, 22.5°, 24.2°, 25.3° and 28.6°, under mild conditions, wherein a crude titanylphthalocyanine having an α-form polymorph is used as a starting material. Therefore, the present invention can control crystallization of the resulting titanylphthalocyanine. Furthermore, the present invention can provide an electrophotographic photoreceptor comprising a charge generating material of the α-form titanylphthalocyanine which has excellent photosensitive characteristics. The resulting titanylphthalocyanine having α-form polymorph according to the present method has a lower crystallization degree than that of the titanylphthalocyanine resulted from the conventional method. Therefore, the present invention can provide an electrophotographic photoreceptor having excellent primary characteristics as a photoreceptor, particularly in electrification characteristics, such as higher initial charging amount, smaller dark decay rate, improved charge remaining property, etc.

DETAILED DESCRIPTION OF THE INVENTION

Detailed Description of the Preferred Embodiments

The present invention relates to a method for producing an α-form titanylphthalocyanine represented by the formula (1):

(1)

which has a peak at a Bragg angle (2θ±0.2°) in X-ray diffraction spectrum with CuK α-ray: 7.5°, 10.2°, 12.6°, 13.2°, 15.1°, 16.3°, 17.3°, 18.3°, 22.5°, 24.2°, 25.3° and 28.6°, wherein the method includes steps of:

(I) subjecting a crude titanylphthalocyanine having an α-form polymorph to an acid pasting treatment, and then filtering and washing with water to give a water-containing wet cake, and then subjecting the wet cake to drying and crushing to give a low crystalline titanylphthalocyanine;

(II) adding a dispersing aid to the low crystalline titanylphthalocyanine and dispersing at room temperature, in DMF, to prepare a desired polymorph; and (III) filtering, washing, and drying under a reduced pressure.

Hereinafter, the method for producing the titanylphthalocyanine having the α-form polymorph according to the present invention is described in detail.

In the method for producing the titanylphthalocyanine having the α-form polymorph according to the present invention, a starting titanylphthalocyanine having an α-form polymorph (hereinafter, which is referred to as a crude titanylphthalocyanine) includes, but in not particularly limited to, for example, any conventional crude α-form titanylphthalocyanine which can be produced or synthesized by a conventional method known to those skilled in the art, such as an urea synthetic method (i.e., Weiller method) or a phthalonitrile synthetic method. The phthalonitrile synthetic method is more preferable as a method for preparing the starting titanylphthalocyanine. Generally, the phthalonitrile method can provide a starting titanylphthalocyanine in a higher yield and in a higher purity than those obtained in the other method such as an urea synthetic method.

Generally, the crude titanylphthalocyanine having α-form polymorph, which can be preferably used as a starting titanylphthalocyanine, can be prepared by a known method including a condensation of phthalonitrile with a metal compound (e.g., titanium tetrachloride) in an aromatic solvent having a high boiling point (e.g., quinoline, α- or β-chloronaphthalene, α-methylnaphthalene and nitrobenzene) to give a titanylphthalocyanine; and then washing the resulting titanylphthalocyanine with a solvent such as DMF (dimethylformamide).

According to the present invention, the method for producing the α-form titanylphthalocyanine includes a step of subjecting a crude titanylphthalocyanine having an α-form polymorph to an acid pasting treatment, and then filtering and washing with water to give a water-containing wet cake, and then subjecting the resulting water-containing wet cake to drying and/or crushing to give a low crystalline titanylphthalocyanine [hereinafter, which is referred to as step (I)].

Step (I) includes a step of subjecting a crude titanylphthalocyanine as a starting material to an acid pasting treatment (hereinafter, which is referred to as AP treatment) according to a conventional method known to those skilled in the art. The acid pasting treatment is a routine procedure for purifying or pulverizing the crude titanylphthalocyanine as a starting material. Generally, the acid pasting treatment includes procedures of dissolving a titanylphthalocyanine into an acid such as concentrated sulfuric acid; and then pouring the resulting solution into a large amount of water to reprecipitate the titanylphthalocyanine.

Herein, specifically, the crude titanylphthalocyanine is dissolved into an acid such as concentrated sulfuric acid. If necessary, insoluble ingredients are to be removed off by means of filtration, etc. The resulting solution and/or filtrate is added dropwise to a large amount of water, which is adequately cooled, or a large amount of iced water, with regard to heat generation, in order to precipitate the titanylphthalocyanine.

Amount of the acid to be used for the acid pasting treatment includes, but is not particularly limited to, an amount giving an appropriate paste suitable for the following purification and/or pulverization.

Preferably, the acid to be used for the acid pasting treatment includes concentrated sulfuric acid. In a case that the concentrated sulfuric acid is used as the acid, the concentrated sulfuric acid has a concentration generally within a range of from 80 to 100%, and preferably within a range of from 95 to 100%. An amount of the concentrated sulfuric acid to be used includes, but is not particularly limited to, an amount giving an appropriate paste suitable for the following purification and/or pulverization. The acid pasting treatment can be carried out only in the presence of an acid and water, and therefore it is convenient.

Subsequently, the precipitated titanylphthalocyanine is subjected to filtering and washing with water in order to provide a water-containing wet cake having water-content within a rage of from 50 to 95%. It is preferable that these filtering and water-washing procedures are repeated to allow the resulting filtrate to be neutralized. In such filtering and water-washing procedures, it is preferable that water such as pure water, distilled water and ion-exchange water is only used, as a washing, since water can facilitate the filtering procedure.

Subsequently, the water-containing wet cake resulted from the acid pasting treatment is dried and/or crushed to provide a low crystalline titanylphthalocyanine. An apparatus to be used for the drying includes, but is not particularly limited to, conventional drying devices known to those skilled in the art. An apparatus to be used for the crushing includes, but is not particularly limited to, conventional crushing devices known to those skilled in the art, such as a flushing mill, a feather mill, a ball mill, sand mill, an attritor, etc. The water-containing wet cake, if it is in a small amount, may be crushed in a device such as mortar, etc.

Figure 2:
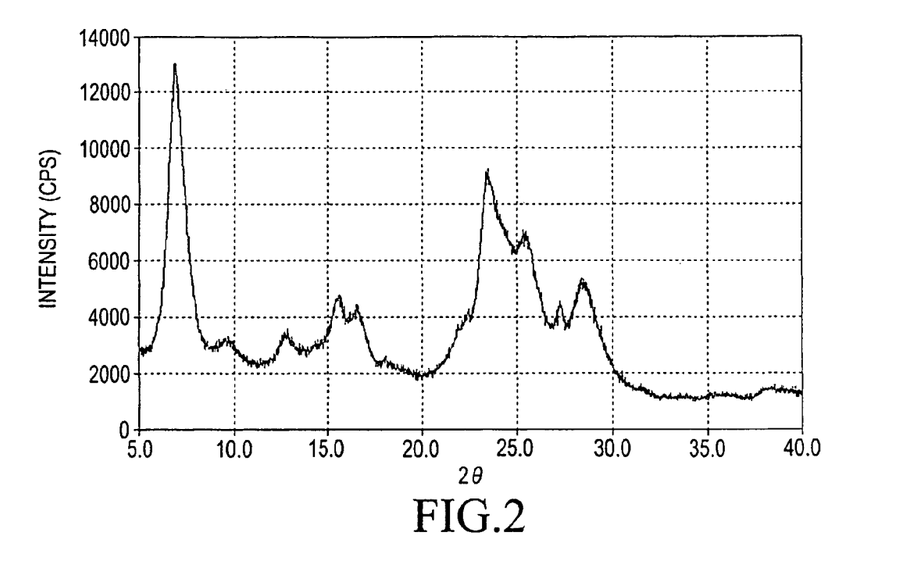
FIG. 2 is an X-ray diffraction spectrum of low crystalline titanylphthalocyanine after acid pasting treatment.

The acid pasting treatment, the subsequent filtering and water-washing, and drying and/or crushing can provide the low crystalline titanylphthalocyanine and it is a novel intermediate. For example, as shown in FIG. 2, the low crystalline titanylphthalocyanine has a peak at a Bragg angle (2θ±0.2°) in X-ray diffraction spectrum with CuK α-ray: 7.0°, 15.6°, 23.5° and 28.4°. It is found that the α-form titanylphthalocyanine according to the present invention can be prepared via the novel intermediate which is different from that the intermediate for the titanylphthalocyanine obtained in a conventional production method. The step (I) including the acid pasting treatment; the filtering and the water-washing to give the water-containing wet cake; and the drying and/or crushing of the water-containing wet cake can facilitate the following step (II) of transformation with DMF.

According to the present invention, the method for producing the α-form titanylphthalocyanine further includes a step of adding a dispersing aid to the low crystalline titanylphthalocyanine and dispersing at room temperature, in DMF, to prepare a polymorph [hereinafter, which is referred to as step (II): transformation]. Herein, the transformation step with DMF can appropriately control crystallinity and particle size of the resulting titanylphthalocyanine.

The dispersing aid to be used in the transformation step includes, but is not particularly limited to, for example, glass beads, steel beads, zirconia beads, alumina beads, etc. Glass beads are preferable for the dispersing aid to be used in the transformation step. Particle size of the dispersing aid is generally within a range of from 0.1 to 10 mm, and preferably within a range of from 0.2 to 5 mm. The dispersing aid is used in an amount within a range of 50 to 150%, and preferably within a range of from 80 to 120%, relative to DMF as a basis of volume, but this amount is not particularly limited.

A apparatus to be used for the transformation step according to the present invention includes, but is not particularly limited to, a conventional reaction vessel and a conventional reaction tank known to those skilled in the art, which can be used in a conventional synthetic reaction. There can be used a conventional dispersing device known to those skilled in the art, such as a sand mill, a ball mill, an attritor, a paint shaker, etc.

The transformation step is carried out at room temperature (usually within a range of from 20 to 35° C.) for a time within a range of from 10 to 80 hours, and preferably within a range of from 30 to 70 hours. If time for the transformation step is less than 10 hours, the formation of the desired polymorph is insufficient. Whereas, even if time for the transformation step is more than 80 hours, generally, significant effects cannot be asserted. This transformation procedure can facilitate the growth of the polymorph according to the present invention. Therefore, the resulting titanylphthalocyanine comprising α-form polymorph can provide excellent photosensitive characteristics. Herein, the transformation procedure is sometimes referred to as "dispersing at room temperature".

The dispersing aid is removed off with a removing means after the transformation procedure. The removing means includes, but is not particularly limited to, those can remove off the used dispersing aid only. It is preferable to use a sieving screen having pores each of which has a size within a range of from 100 to 200 μm. If the size is less than 100 μm, time is terribly taken long to remove off the dispersing aid and it provides a low yield. Whereas, if the size is more than 200 μm, there may be a contamination of fragments of the dispersing aid into the resulting titanylphthalocyanine, which may deteriorate the photosensitive characteristics thereof.

The method for producing the α-form titanylphthalocyanine according to the present invention further includes a step of filtering, washing, and drying at a reduced pressure [hereinafter, which is referred to as step (III)]. Filtration of the dispersion free of the dispersing aid, and washing of the resulting filtration residue can provide the titanylphthalocyanine having α-form polymorph of the present invention. The filtration is not particularly limited. The washing can be carried out with an appropriate solvent such as an organic solvent (e.g., DMF, THF, methanol, etc.), ion-exchange water, distilled water, etc. If the resulting titanylphthalocyanine according to the present invention is applied to an electrophotographic photoreceptor, it is preferable that the resulting titanylphthalocyanine has a high purity. Therefore, the production method according to the present invention may further include any purification procedures.

It is preferable that the titanylphthalocyanine resulted from the filtering and washing is dried at a reduced pressure. The drying is carried out under the following conditions. For example, drying temperature is generally within a range of from 40 to 100° C., and preferably within a range of from 50 to 70° C., and drying period is within a range of from 15 to 30 hours. After drying, the resulting dried mass of the titanylphthalocyanine can be crushed. The resulting titanylphthalocyanine having α-form polymorph according to the present production method can be applied, as a charge generating material, to an electrophotographic photoreceptor.

The production method according to the present invention can conveniently provide a desired titanylphthalocyanine, since the present method does not include any complicated processes, such as a thermal treatment and vigorous washing with a solvent with heating, as described above.

Hereinafter, the electrophotographic photoreceptor according to the present invention is described in detail. The electrophotographic photoreceptor according to the present invention is characterized in that the α-form titanylphthalocyanine obtainable/obtained according to the present production method is used as a charge generating material. Therefore, the present electrophotographic photoreceptor comprising a charge generating material of the α-form titanylphthalocyanine obtained/obtainable according to the present production method can provide excellent electrification characteristics, excellent sensitivity, excellent durability and excellent digital photosensitive characteristics.

The electrophotographic photoreceptor comprises a photoreceptor layer comprising the titanylphthalocyanine having α-form polymorph prepared according to the present inventive process, wherein the photoreceptor layer may have a one-layer structure or a two-layer structure comprising a charge generating layer and a charge transferring layer. In order to significantly present the photosensitive characteristics due to the polymorph of the titanylphthalocyanine, it is preferable to apply the titanylphthalocyanine to a photoreceptor having a two-layer structure or a multi-layer structure, wherein each function can be provided in each layer, i.e., in a function separated type, and wherein a slight amount of generated charges can be intercepted, and therefore the electric charge is effectively transferred to the surface of the photoreceptor without adversely effecting on each function in each layer.

Such photoreceptor in a function separated type can be formed, for example, by laminating a thin charge generating layer and a thin charge transferring layer thereon, in this order, on a conductive support. A material for the conductive support includes a metal such as aluminum and nickel, a metal deposition film thereof, etc. The conductive support can be manufactured into a form of drum, sheet or belt.

A method for adopting the titanylphthalocyanine to an electrophotographic photoreceptor includes an initial step of forming a charge generating layer comprising a charge generating material [i.e., CG material (CGM)] of the α-form titanylphthalocyanine according to the present invention, in a preferable form of a thin film, on a conductive support. Herein, the charge generating layer can be formed by depositing the titanylphthalocyanine on the conductive support, or by applying a coating dispersion containing the charge generating material to the conductive support, wherein the coating dispersion can be prepared by dispersing the charge generating material in a solvent to which a binder resin has been dissolved.

The method for dispersing the titanylphthalocyanine to prepare a coating dispersion includes a conventional dispersing method by means of a ball mill, a sand mill, a paint shaker, or the like.

An applicator for applying the charge generating layer includes, but is not particularly limited to, for example, a bar coater, a dip coater, a spin coater, a roller coater, and the like, each of which can be appropriately employed. Drying of the applied layer may be carried out, for example, at a temperature within a range of from 30 to 200° C. for 5 minutes to 5 hours with or without an air stream.

The solvent for preparing the coating dispersion includes, but is not particularly limited to, known organic solvents, which can uniformly disperse the titanylphthalocyanine without dissolving the titanylphthalocyanine, and if necessary which can dissolve the binder resin. Examples of the solvent include alcohol solvents such as methanol, ethanol, isopropanol and butanol; aromatic solvents such as toluene, xylene and tetralin; halogen-containing solvents such as dichloromethane, chloroform, trichloroethylene and carbon tetrachloride; ester solvents such as ethyl acetate and propyl acetate; ether solvents such as ethylene glycol monoethyl ether, dioxane and tetrahydrofuran; ketone solvents such as cyclohexanone, acetone, methyl ethyl ketone and methyl isobutyl ketone; dimethylformamide; dimethylsulfoxide; etc.

The binder resin can be selected from various insulating resins. Preferable binder resin includes condensed resins such as polycarbonates, polyacrylates, polyesters and polyamides; addition polymers such as polystyrenes, styrene/acrylic copolymers, polyacrylates, polymethacrylates, polyvinylbutyrals, polyvinyl alcohols, polyacrylonitriles, polyacryl/butadiene copolymers, polyvinyl chlorides and vinyl chloride/vinyl acetate copolymers; insulating resins such as poly-N-vinylcarbazoles and polyvinylanthracenes; polysulfones; polyethersulfones; silicone resins; epoxy resins; urethane resins; etc. The binder resin may be used in an appropriate combination thereof. Herein, the binder resin which can be used in the present invention is not limited to the above exemplified resins.

The amount of the above-described binder resin to be used is within a range of from 0.1 to 3, in a weight ratio, relative to the weight to the charge generating material. If the weight ratio is more than 3, the concentration of the charge generating material in the charge generating layer may be decreased to provide a deteriorated sensitivity. Film thickness of the charge generating layer is generally no more than 10 μm, and preferably, in a practice, within a range of from 0.05 to 5.0 μm.

Subsequently, a charge transferring layer comprising a charge transferring material [i.e., CT material (CTM)] in a preferable form of a thin film can be formed on the resulting charge generating layer. A method for forming the thin film includes the similar procedures to those in the applying method for the charge generating layer. Herein, the charge transferring material can be dissolved, if necessary together with a binder resin, in a solvent, and the resulting coating solution can be uniformly applied on the charge generating layer and then subjected to drying.

The charge transferring material includes, but is not particularly limited to, known compounds such as an oxadiazoles, pyrazolines, pyrazoles, hydrazones, triazines, quinazolines, triarylamines, methaphenylenediamines, carbazoles, indoles, imidazoles, styryls, styryltriarylamines, butadienes, etc.

Preferably, the binder resin and solvent for preparing the charge transferring layer include those above-exemplified in the preparation of the charge generating layer, etc.

The amount of the above-described binder resin to be used is within a range of from 0.1 to 5, in a weight ratio, relative to the weight of the charge transferring material. If the weight ratio is more than 5, the concentration of the charge transferring material in the charge transferring layer may be decreased to provide a deteriorated sensitivity. The film thickness of the charge transferring layer is generally within a range of from 5 to 100 μm. If the film thickness is more than 100 μm, the transferring of the electric charge takes much more time, and the electric charge can be trapped in a certain high probability, and therefore which can cause an undesired deteriorated sensitivity.

EXAMPLES

Hereinafter, the present invention is further described in detail in the following Examples, which are not intended to limit the present invention.

Example 1

Step (1-A): Preparation of α-Form Titanylphthalocyanine as Starting Material (i.e., Crude Titanylphthalocyanine Having α-Form Polymorph)

100 g (0.780 mol) of o-phthalonitrile and 1 L of quinoline were charged into a 2 L separable flask. The mixture was stirred under a nitrogen atmosphere. 84.98 g (0.448 mol) of titanium tetrachloride was added to the mixture. Subsequently, the mixture was heated to 180° C. and stirred with heating at the same temperature for 6 hours. After the reaction was completed, the temperature in the system was allowed to be decreased to 150° C., and then the reaction mixture was filtered with heating. Subsequently, 1 L of DMF heated (at 110° C.) was added thereto and the resulting residue was washed.

The resulting wet cake was added to 640 mL of DMF and dispersed at 130° C. for 2 hours. The dispersion was filtered with heating at 130° C. Subsequently, 1 L of DMF was added thereto and the resulting residue was washed. This routine procedure was repeated four times. Subsequently, 1 L of methanol was added thereto and the resulting residue was washed. The resulting wet cake was dried at 40° C. under a reduced pressure to give a blue solid (in producing amount: 86.3 g and yield: 76.8%).

Figure 1:
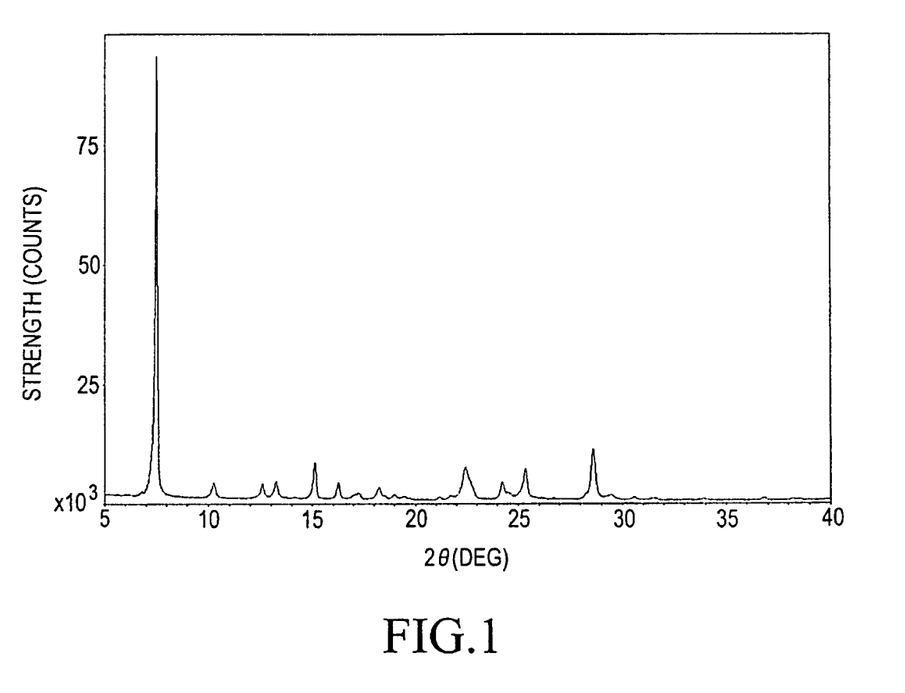
FIG. 1 is an X-ray diffraction spectrum of a crude titanylphthalocyanine having α-form polymorph.

X-Ray diffraction chart of the resulting crude titanylphthalocyanine is shown in FIG. 1.

Step (1-B): Acid Pasting Treatment 900 g of concentrated sulfuric acid was cooled to no more than 3° C. in an ice-methanol bath. 30 g (52 mmol) of the above-prepared blue solid was added into the concentrated sulfuric acid with keeping the temperature at no more than 5° C. The reaction mixture was stirred at no more than 5° C. for 1 hour, and then the reaction mixture was added dropwise to 9000 mL of water and 1000 mL of ice so that the temperature in the system did not exceed 5° C. The mixture was dispersed at room temperature for 2 hours, and then the dispersion was allowed to be left and past trough a filter. The resulting cake was added to 6000 mL of water, and then dispersed at room temperature for 1 hour. Subsequently, the dispersion was allowed to be left and past trough a filter. This routine procedure was repeated three times. The resulting cake was added into 5000 mL of water, dispersed at room temperature for 1 hour, and then allowed to be left and past trough a filter. This routine procedure was repeated twice, and then 2000 mL of ion-exchange water was added thereto and the resulting residue was washed. Once pH was >6.0 and electroconductivity was <20 μS, the wet cake was taken up.

The resulting wet cake was dried and crushed to give a powder of blue solid. This blue solid was subjected to an X-ray diffraction analysis with CuK α-ray. It was found that the blue solid was a low crystalline titanylphthalocyanine having peaks at Bragg angles (2θ±0.2°) in X-ray diffraction spectrum with CuK α-ray: 7.0°, 15.6°, 23.5° and 28.4° (in producing amount: 26.0 g).

X-Ray diffraction chart of the low crystalline titanylphthalocyanine is shown in FIG. 2.

Step (1-C): Transformation 12.0 g of the blue powder of the low crystalline titanylphthalocyanine resulted from the above-described step (1-B), 200 mL of DMF, 200 mL of glass beads each of which has a particle size of 0.5 mmφ were charged into a 500 mL beaker. The mixture was subjected to dispersing at room temperature (at 25° C.) for 39 hours. The beads were removed off to give a dispersion. The dispersion was filtered at a reduced pressure to give a cake. The cake was washed with addition of 200 mL of DMF and then 200 mL of methanol. The resulting cake was dried at a reduced pressure at 70° C. for 24 hours to give a solid. The solid was crushed or sieved through a sieving screen having pores each of which has a size of 150 μm to give a titanylphthalocyanine having α-form polymorph having a peak at a Bragg angle (2θ±0.2°) in X-ray diffraction spectrum with CuK α-ray: 7.5°, 10.2°, 12.6°, 13.2°, 15.1°, 16.3°, 17.3°, 18.3°, 22.5°, 24.2°, 25.3° and 28.6° (in producing amount: 11.0 g).

Figure 3:
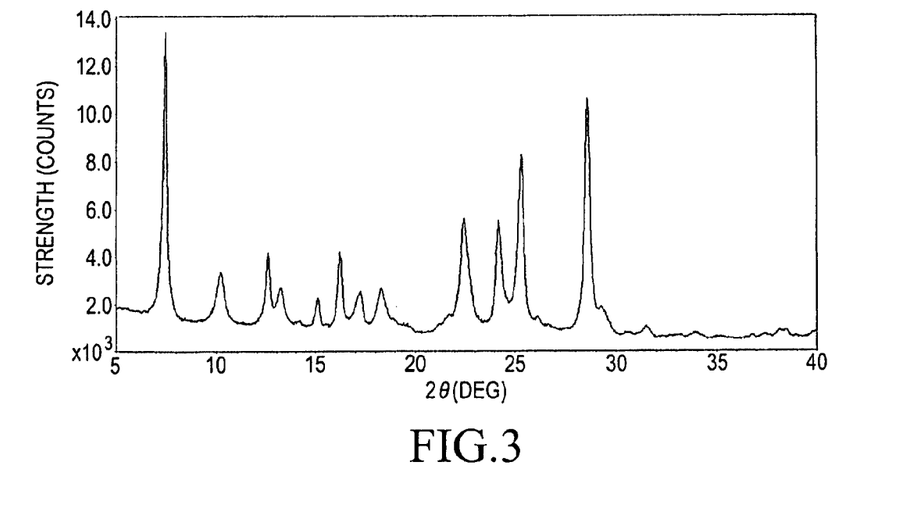
FIG. 3 is an X-ray diffraction spectrum of α-form titanylphthalocyanine according to the present invention (Example 1).

FIG. 3 shows X-ray diffraction spectrum of the titanylphthalocyanine resulted from the Example 1.

Example 2

Step (2-A): Preparation of α-Form Titanylphthalocyanine as Starting Material The similar procedures to those described in the above step (1-A) in the Example 1 were employed with the proviso that each material was used in 40 times in its amount to give a blue solid (in producing amount: 2850 g).

Step (2-B): Acid Pasting Treatment

The similar acid pasting procedures to those described in the above step (1-B) in the Example 1 including the drying and the crushing or sieving procedures were employed with the proviso that each material was used in 40 times in its amount to give a low crystalline titanylphthalocyanine.

Step (2-C): Transformation 448.0 g of the blue powder of the low crystalline titanylphthalocyanine resulted from the above-described step (2-B), 7.5 L of DMF, and 8.2 L of glass beads each of which has a particle size of 0.5 mmφ were charged into a 20 L enamel tank. The mixture was subjected to dispersing at room temperature (at 25° C.) for 66 hours. The beads were removed off to give a dispersion. The dispersion was filtered at a reduced pressure to give a cake. The cake was washed with addition of 4.0 L of DMF and then 4.0 L of methanol. The resulting cake was dried at a reduced pressure at 70° C. for 24 hours to give a solid. The solid was crushed or sieved through a sieving screen having pores each of which has a size of 150 μm to give a titanylphthalocyanine having α-form polymorph (in producing amount: 429.3 g).

X=ray diffraction spectrum of the titanylphthalocyanine resulted from the Example 2 corresponds to that of FIG. 3.

Comparative Example 1

According to the Example 1, Comparative Example 1 was carried out in similar procedures to those described in the above step (1-C) in the Example 1 with the proviso that the dispersing was carried out at 120° C. with heating instead of dispersing at room temperature in the Example 1. As a result, high crystalline α-form titanylphthalocyanine was produced (in producing amount: 10.8 g).

Figure 4:
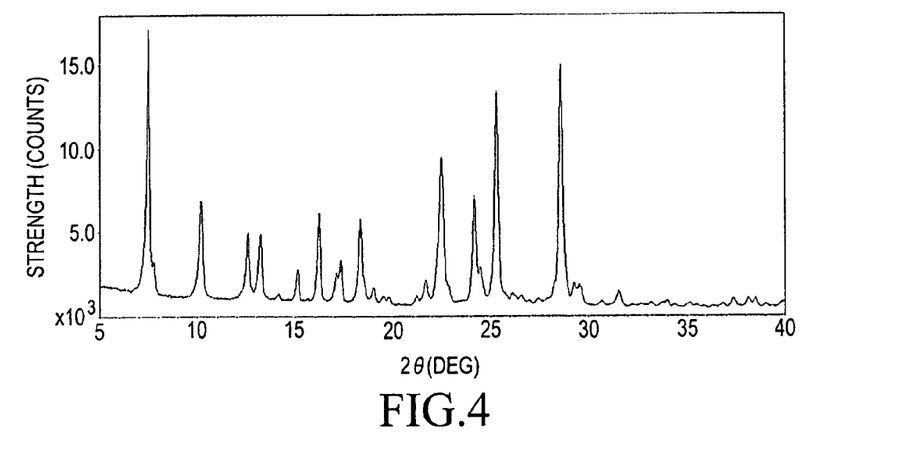
FIG. 4 is an X-ray diffraction spectrum of titanylphthalocyanine (in α-form polymorph) according to Comparative Example 1.

X-ray diffraction spectrum of the titanylphthalocyanine resulted from the Comparative Example 1 is shown in FIG. 4.

Comparative Example 2

According to the Example 1, Comparative Example 2 was carried out in similar procedures to those described in the above step (1-C) in the Example 1 with the proviso that the glass beads having 0.5 mmφ particle size were not employed. As a result, titanylphthalocyanine in a combination of α-form crystal and C-form crystal (in a part) was produced (in producing amount: 11.7 g).

Figure 5:
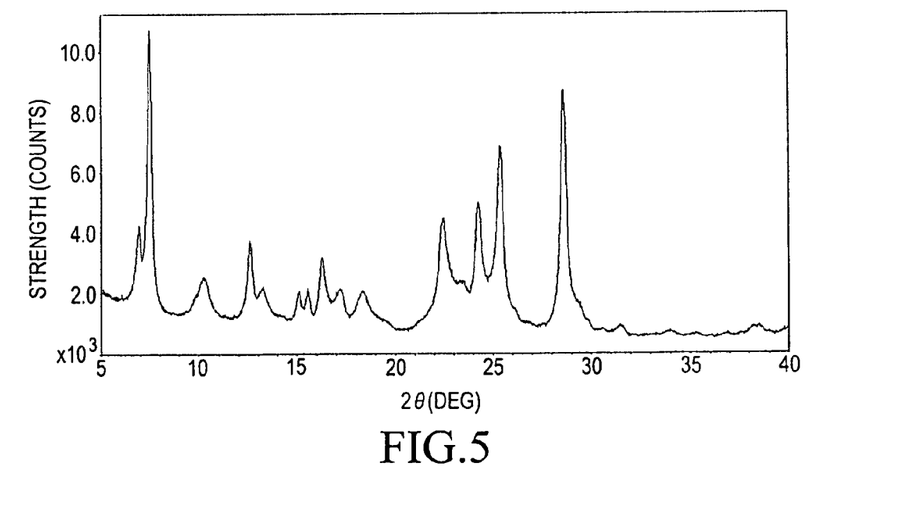
FIG. 5 is an X-ray diffraction spectrum of titanylphthalocyanine (in a combination of α-form and C-form polymorphs) according to Comparative Example 2.

X-ray diffraction spectrum of the titanylphthalocyanine resulted from the Comparative Example 2 is shown in FIG. 5.

Comparative Example 3

According to the Example 1, Comparative Example 3 was carried out in similar procedures to those described in the above step (1-C) in the Example 1 with the proviso that the glass beads having 0.5 mmφ particle size were not employed and the dispersing was carried out at 120° C. As a result, titanylphthalocyanine in a combination of C-form crystal and α-form crystal (in a part) was produced (in producing amount: 11.4 g).

Figure 6:
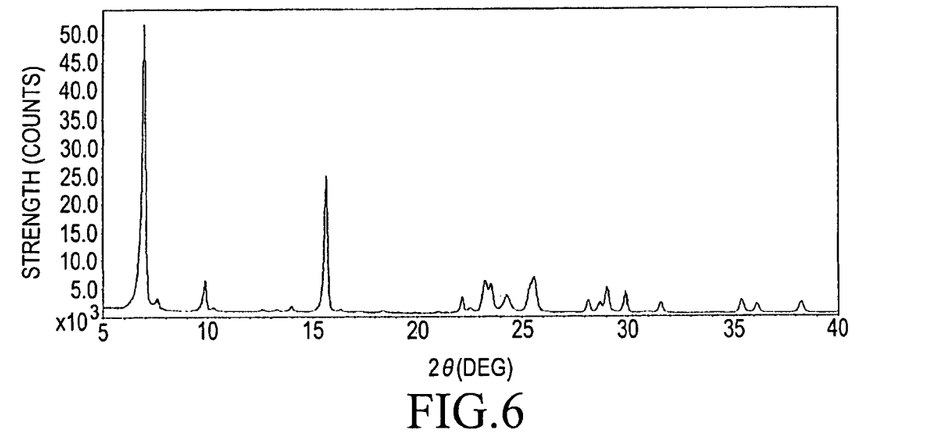
FIG. 6 is an X-ray diffraction spectrum of titanylphthalocyanine (in a combination of α-form and C-form polymorphs) according to Comparative Example 3.

X-ray diffraction spectrum of the titanylphthalocyanine resulted from the Comparative Example 3 is shown in FIG. 6.

Comparative Example 4

According to the Example 1, Comparative Example 4 was carried out in similar procedures to those described in the above step (1-C) in the Example 1 with the proviso that the water-containing wet cake of the low crystalline titanylphthalocyanine resulted from the above-described step (1-B) was not dried and used as it was. As a result, titanylphthalocyanine in a combination of C-form crystal and α-form crystal (in a part) was produced (in producing amount: 12.2 g).

Figure 7:
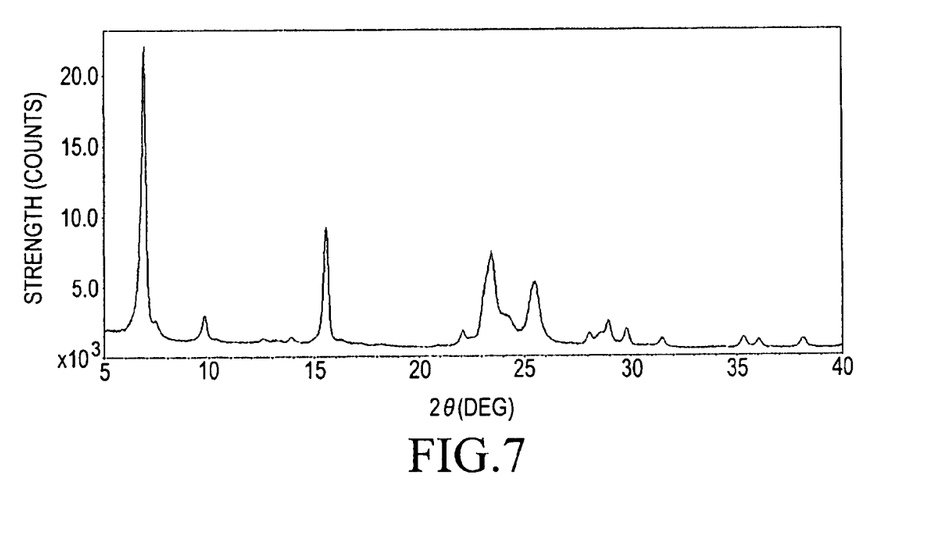
FIG. 7 is an X-ray diffraction spectrum of titanylphthalocyanine (in a combination of α-form and C-form polymorphs) according to Comparative Example 4.

X-ray diffraction spectrum of the titanylphthalocyanine resulted from the Comparative Example 4 is shown in FIG. 7.

Comparative Example 5

According to the Example 1, Comparative Example 5 was carried out in similar procedures to those described in the above step (1-C) in the Example 1 with the proviso that the glass beads having 0.5 mmφ particle size were not employed and the water-containing wet cake of the low crystalline titanylphthalocyanine resulted from the above-described step (1-B) was not dried and used as it was. As a result, C-form titanylphthalocyanine was produced, which has a peak at a Bragg angle (2θ±0.2°) in X-ray diffraction spectrum with CuK α-ray: 6.9°, 15.6°, 23.5°, 25.4° and 28.6° (in producing amount: 11.8 g).

Figure 8:
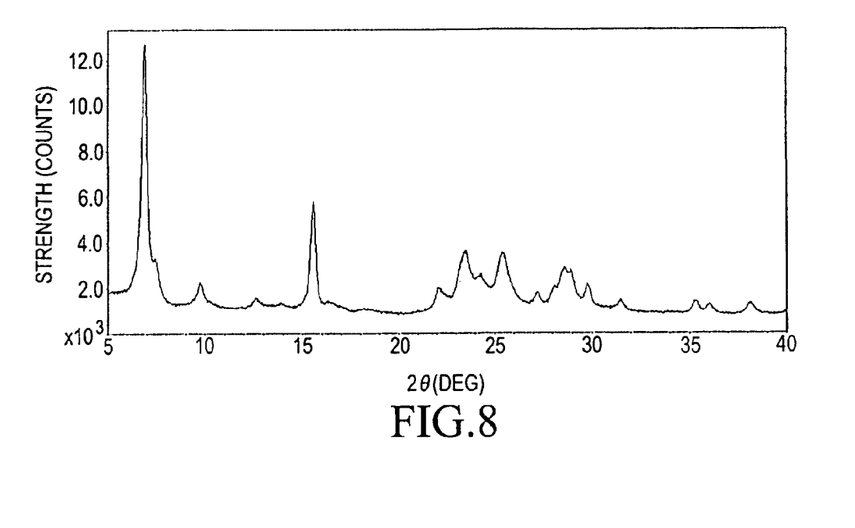
FIG. 8 is an X-ray diffraction spectrum of titanylphthalocyanine (in C-form polymorph) according to Comparative Example 5.

X-ray diffraction spectrum of the titanylphthalocyanine resulted from the Comparative Example is shown in FIG. 8.

Comparative Example 6

According to the Example 1, Comparative Example 6 was carried out in similar procedures to those described in the above step (1-C) in the Example 1 with the proviso that the glass beads having 0.5 mmφ particle size were not employed, the water-containing wet cake of the low crystalline titanylphthalocyanine resulted from the above-described step (1-B) was not dried and used as it was, and the dispersing was carried out at 120° C. Similarly, post-treatments after the transformation were carried out. As a result, C-form titanylphthalocyanine was produced, which has a peak at a Bragg angle (2θ±0.2°) in X-ray diffraction spectrum with CuK α-ray: 6.9°, 15.6°, 23.5°, 25.4° and 28.6° (in producing amount: 11.8 g).

Figure 9:
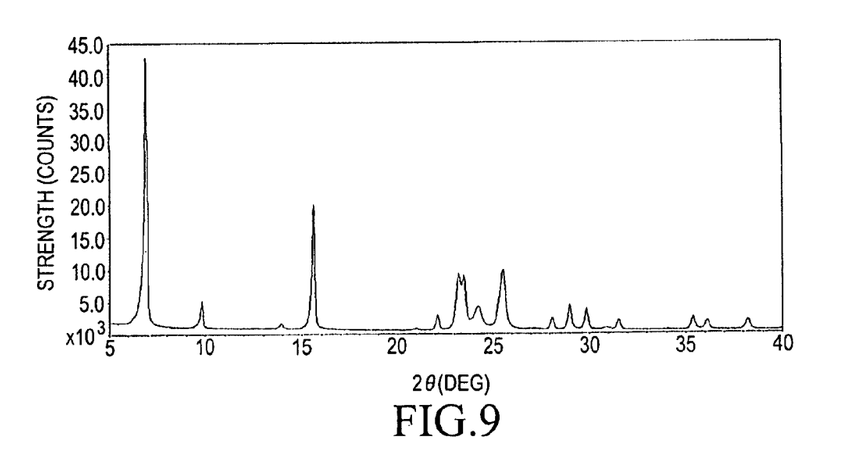
FIG. 9 is an X-ray diffraction spectrum of titanylphthalocyanine (in C-form polymorph) according to Comparative Example 6.

X-ray diffraction spectrum of the titanylphthalocyanine resulted from the Comparative Example 6 is shown in FIG. 9.

The following Table 1 shows conditions for the transformation in the Examples 1 and 2 and the Comparative Examples 1-6 as well as the crystal form of the resulted titanylphthalocyanine (i.e., polymorph).

TABLE 1

Conditions for transformation and crystal form of titanylphthalocyanine in Examples 1 and 2 and Comparative Examples 1-6

| | Titanylphthalocyanine after AP treatment | | DMF (ml) | Temperature (°C.) | Beads (ml) | Crystal form | Note |
|---|---|---|---|---|---|---|---|
| | Wet* (g) | Dry (g) | | | | | |
| Example 1 | | 12.0 | 200 | 25 | 200 | α | Low Crystallinity |
| Example 2 | | 448.0 | 7500 | 25 | 8200 | α | Low Crystallinity |
| Comparative Example 1 | | 12.0 | 200 | 120 | 200 | α | High Crystallinity |
| Comparative Example 2 | | 12.0 | 200 | 25 | 0 | α + C | |
| Comparative Example 3 | | 12.0 | 200 | 120 | 0 | α + C | |
| Comparative Example 4 | 43.7 (12.0) | | 200 | 25 | 200 | α + C | |
| Comparative Example 5 | 43.7 (12.0) | | 200 | 25 | 0 | C | |
| Comparative Example 6 | 43.7 (12.0) | | 200 | 120 | 0 | C | |

*Calculated as a dried product

It can be seen from the Table 1 that the Examples 1 and 2 and the Comparative Example 1 can provide α-form titanylphthalocyanine. There is a difference in degree of crystallization (i.e., crystallinity) between the titanylphthalocyanine of the Example 1 or 2 and the titanylphthalocyanine of the Comparative Example 1. The Comparative Examples 2-4 can not provide α-form titanylphthalocyanine in a single crystal, but provide a combination of C-form crystal and α-form crystal thereof. The Comparative Examples 5 and 6 can not provide α-form titanylphthalocyanine, but provide C-form crystal of the titanylphthalocyanine in a single crystal.

Subsequently, an exemplified method for producing an electrophotographic photoreceptor comprising α-form titanylphthalocyanine prepared according to the present inventive process is described hereinafter. Herein, the electrophotographic photoreceptor according to the present invention is not limited to these examples.

Example 3

0.2 g of the titanylphthalocyanine crystal prepared in the Example 1; 0.2 g of polyvinylbutyral resin (under a trade name: Esrek BH-3, manufactured by Sekisui Chemical Co., Ltd.); 50 g of 3 mmφ glass beads; and 59.6 g of cyclohexanone were charged into a wide-mouthed bottle, and then subjected to 3 hour milling with a paint shaker to prepare a coating dispersion for forming a photoreceptor layer. This coating dispersion was applied on an aluminum plate by using a bar coater to give a film in a film thickness of 0.5 μm, and then the film was dried in air to form a charge generating layer.

Subsequently, 4.5 g of p-(N,N'-diphenylamino)benzaldehyde-N'-methyl-N'-phenylhydrazine (under a trade name: CT-501, manufactured by Fuji Photo film Co., Ltd.) as a charge transferring material (CTM); 4.5 g of a polycarbonate resin (under a trade name: Panlight L-1250, manufactured by Teijin Limited); and 51 g of methylene chloride were charged into a wide-mouthed bottle, and then ultrasonically dispersed to prepare an uniform solution. This solution was applied on the charge generating layer by using a bar coater, and then dried at 80° C. for 3 hours to form a charge transferring layer in a film thickness of 60 μm on the charge generating layer. The prepared plate is an organic photoreceptor (specimen).

Example 4

An organic photoreceptor was prepared according to the Example 3 with the proviso that the crystal of the titanylphthalocyanine according to the Example 2 was employed instead of the crystal of the titanylphthalocyanine according to the Example 1 which was employed in the Example 3.

Comparative Example 8

An organic photoreceptor was prepared according to the Example 3 with the proviso that the crystal of the titanylphthalocyanine according to the Comparative Example 1 was employed instead of the crystal of the titanylphthalocyanine according to the Example 1 which was employed in the Example 3.

With regard to the photoreceptors manufactured in the above-described Examples 3 and 4 and the Comparative Example 8, the photosensitive characteristics were determined. A measuring device for electrostatic testing (under a trade name: Paper Analyzer EPA-8200, manufactured by Kawaguchi Denki Co., Ltd.) was used for the measurement. Herein, charged potential (Vmax) (V), dark decay rate (DDR) (%), residual potential (Vre.) (V) and half decay exposure (E1/2) (lux·s) (as sensitivity) were measured and evaluated, wherein each photoreceptor was initially charged at a voltage of −0.8 kV (in STAT 3 mode), allowed to be left in a dark place for 2 seconds, and then irradiated with 5.0 lux white light for 10 seconds. The measurement results are shown in the following Table 2.

The dark decay rate (DDR) (%) was determined by the following equation, wherein the surface potential immediately after charging ($V_0$=Vmax) and the surface potential after leaving 2 seconds in dark place ($V_2$) were measured.

$$\text{Dark decay rate } (\%) = 100 \times (V_0 - V_2)/V_0$$

Evaluation

The evaluation basis for electrification characteristics (such as chargeability) in the following Table 2 is as follows.

Excellent (○): Absolute charged potential (Vmax) is no less than 600 V and dark decay rate is less than 10.

Terrible (X): Absolute charged potential (Vmax) is less than 600 V and dark decay rate is 10 or more.

The evaluation basis for sensitivity in the following Table 2 is as follows.

Excellent (○): Half decay exposure (E1/2) (Lux·s) (as sensitivity) is less than 2

Terrible (X): Half decay exposure (E1/2) (Lux·s) (as sensitivity) is 2 or more.

TABLE 2

Evaluation of photosensitive characteristics

|  | CGM | Vmax (V) | DDR (%) | Vre. (V) | E½ (Lux · s) | Electrification Characteristics Evaluation | Sensitivity Evaluation |
|---|---|---|---|---|---|---|---|
| Ex. 3 | Ex. 1 | −687.0 | 7.13 | −43.7 | 1.69 | ○ | ○ |
| Ex. 4 | Ex. 2 | −696.0 | 6.90 | −38.0 | 1.63 | ○ | ○ |
| Comp. Ex. 8 | Comp. Ex. 1 | −374.3 | 14.60 | −2.3 | 2.59 | X | X |

According to the Table 2, it can be seen that the electrophotographic photoreceptor comprising the charge generating material of the α-form titanylphthalocyanine obtained according to the present inventive process has excellent photosensitive characteristics, such as high degree of absolute initial charged potential (Vmax), appropriate dark decay rate (DDR) and appropriate half decay exposure (E1/2) (as sensitivity), even though the electrophotographic photoreceptor contains the titanylphthalocyanine according to the Example 1 or 2 in a different scale, i.e., scale-up was carried out in the Example 2.

Whereas, the electrophotographic photoreceptor of the Comparative Example 8 has poor photosensitive characteristics, such as lower degree of absolute Vmax, almost doubled DDR and no less than about 1.5 times of E1/2 than those of the electrophotographic photoreceptor of the Example 3 or 4

As described above, it is found that the α-form titanylphthalocyanine obtained according to the present inventive process has much superior photosensitive characteristics than those of the conventional titanylphthalocyanine which was prepared (as sensitivity) via a conventional heat treatment (see the Comparative Example 1).

INDUSTRIAL APPLICABILITY

The present invention can provide a method for conveniently producing an α-form titanylphthalocyanine under mild conditions. In addition, the present method can be carried out in an industrial scale and has stability. In addition, the α-form titanylphthalocyanine obtained according to the present invention has much superior photosensitive characteristics than those of the conventional α-form titanylphthalocyanine which was prepared via a conventional heat treatment. Therefore, the α-form titanylphthalocyanine of the present invention is useful for a charge generating material. Accordingly, the present invention can provide an electrophotographic photoreceptor having excellent photosensitive characteristics.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising", "having", "including", and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those skilled in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A method for producing an α-form titanylphthalocyanine represented by the formula (I):

(1)

which has a peak at a Bragg angle (2θ±0.2°) in X-ray diffraction spectrum with CuK α-ray: 7.5°, 10.2°, 12.6°, 13.2°, 15.1°, 16.3°, 17.3°, 18.3°, 22.5°, 24.2°, 25.3° and 28.6°, wherein the method includes steps of:

(I) subjecting a crude titanylphthalocyanine having an α-form polymorph to an acid pasting treatment, and then filtering and washing with water to give a water-containing wet cake, and then subjecting the wet cake to drying and crushing to give a low crystalline titanylphthalocyanine;

(II) adding a dispersing aid to the low crystalline titanylphthalocyanine and dispersing at room temperature, in DMF, to prepare a polymorph; and (III) filtering, washing, and drying under a reduced pressure.

2. The method according to claim 1, wherein the law crystalline titanylphthalocyanine has a peak at a Bragg angle (2θ±0.2°) in X-ray diffraction spectrum with CuK α-ray: 7.0°, 15.6°, 23.5° and 28.4°.

* * * * *